(12) United States Patent
Amabile et al.

(10) Patent No.: US 10,098,696 B2
(45) Date of Patent: Oct. 16, 2018

(54) MICROWAVE DEVICE FOR TISSUE ABLATION

(71) Applicant: H.S. - Hospital Service S.P.A., Rome (IT)

(72) Inventors: Claudio Amabile, Cisterna di Latina (IT); Simone Cassarino, Rome (IT); Nevio Tosoratti, Rome (IT)

(73) Assignee: H.S.-Hospital Service S.P.A. (IT)

( * ) Notice: Subject to any disclaimer, the term of this patent is extended or adjusted under 35 U.S.C. 154(b) by 899 days.

(21) Appl. No.: 14/379,390

(22) PCT Filed: Feb. 18, 2013

(86) PCT No.: PCT/IB2013/051312
§ 371 (c)(1),
(2) Date: Aug. 18, 2014

(87) PCT Pub. No.: WO2013/121403
PCT Pub. Date: Aug. 22, 2013

(65) Prior Publication Data
US 2015/0038956 A1    Feb. 5, 2015

(30) Foreign Application Priority Data
Feb. 17, 2012    (IT) .............................. MO2012A0041

(51) Int. Cl.
*A61B 18/18*    (2006.01)
*A61B 18/00*    (2006.01)

(52) U.S. Cl.
CPC ..................... *A61B 18/1815* (2013.01); *A61B 2018/00148* (2013.01); *A61B 2018/00577* (2013.01); *A61B 2018/1869* (2013.01)

(58) Field of Classification Search
CPC ................ A61B 18/18; A61B 18/1815; A61B 2018/00148; A61B 2018/00577; A61B 2018/1869
(Continued)

(56) References Cited

U.S. PATENT DOCUMENTS 4,700,716 A    10/1987    Kasevich et al.
5,129,396 A     7/1992    Rosen et al.
(Continued)

FOREIGN PATENT DOCUMENTS

| EP | 2255742 A1   | 12/2010 |
| IT | MO20050034 A1 | 8/2006 |
| WO | 2006084676 A1 | 8/2006 |

OTHER PUBLICATIONS

International Search Report & Written Opinion Application No. PCT/IB2013/051312 Completed: Jun. 7, 2013; dated Jun. 18, 2013 6 pages.

*Primary Examiner* — Michael Peffley
*Assistant Examiner* — Khadijeh Vahdat
(74) *Attorney, Agent, or Firm* — St Onge Steward Johnston and Reens LLC

(57) ABSTRACT

A microwave device for the ablation of biological tissues including a coaxial antenna, including an internal conductor, surrounded by a layer of dielectric material, an external conductor coaxial to the dielectric metal tip electrically connected to the internal conductor, and a quarter wave impedance transformer including a sleeve made of dielectric material having a proximal end covered with a layer of metal, the metal extending over nearly a quarter wavelength of electromagnetic field in the dielectric at the operating frequency of the device or of odd multiples of the quarter wavelength, the layer of metal material being connected electrically to the external conductor.

13 Claims, 7 Drawing Sheets

(58) Field of Classification Search
USPC .................................................... 606/33–34
See application file for complete search history.

(56) References Cited

U.S. PATENT DOCUMENTS

| | | |
|---|---|---|
| 2003/0088242 A1 | 5/2003 | Prakash et al. |
| 2003/0100894 A1 | 5/2003 | Mahon et al. |
| 2011/0060325 A1 | 3/2011 | Bonn |
| 2011/0118721 A1 | 5/2011 | Brannan |
| 2011/0282336 A1* | 11/2011 | Brannan ............ A61B 18/1815 606/33 |

* cited by examiner

MICROWAVE DEVICE FOR TISSUE ABLATION

FIELD OF THE INVENTION

This invention relates to a microwave device for tissue ablation, in particular an interstitial microwave applicator for hyperthermal treatment of biological tissues, in particular for thermoablation of said tissues.

BACKGROUND OF THE INVENTION

Thermoablation consists of destroying target tissues by increasing the temperature of cells beyond an irreversible damage threshold. This threshold is linked to exposure time at a given temperature; in the case of temperatures comprised between 50° C. and 60° C. the time is a few minutes whereas from 60° C. above cell death is almost instantaneous. The temperature increase is obtained by dispensing energy into the target tissues by more or less invasive applicators. The forms of energy that are commonly used for thermoablation comprise mechanical waves, radio-frequency currents, infrared radiation, and microwaves.

One of the most promising forms of energy for thermoablation is currently microwave energy, which provides an excellent compromise between the efficiency of the energy transfer and the depth of penetration into the biological tissues. The dispatch of microwave energy into tissues intended for thermoablation occurs by percutaneous, endoscopic, laparotomic or laparoscopic insertion of interstitial applicators consisting of a coaxial antenna comprising an internal conductor, a layer of dielectric material that covers the entire length of the internal conductor, an external conductor that coaxially covers the layer of dielectric material and the internal conductor, except for a distal end portion thereof, constituting the radiant end of the antenna. The design of antennas for thermoablation has to consider certain constructional requirements linked to the use that is made thereof, in particular: biocompatibility, great mechanical resistance, spherical coagulative necrosis, a diameter of the antenna that is as small as possible.

The antenna for guaranteeing a spherical coagulative necrosis requires both a radiation figure that is in turn spherical and a cooling system for dissipating the generated heat of the supply line of the antenna. At the operating frequencies of the microwave thermoablation system the transit power through the coaxial cable is characterised by great attenuation to which heating of the coaxial cable corresponds. The heat generated could cause necrosis of the tissues in contact with the external stem of the antenna over the entire length thereof. The presence of a cooling circuit of the supply line enables the heat to be removed and the eccentricity of the necrosis to be thus reduced.

SUMMARY OF THE INVENTION

A common problem of many designs for microwave thermoablation antennas is the elongation of the radiation figure along the antenna supply line, with consequent low sphericity. This elongation can be avoided by different improvements to the antenna design. One of the most common methods of maintaining good confinement of the radiation figure is using a device, called an electromagnetic choke, or merely choke, that creates a quarter-wave impedance transformer ending in a short circuit. The choke is physically a coaxial line consisting of a cylindrical conductor that coaxially surrounds the external conductor of the antenna and is closed in a short circuit thereupon at the proximal end thereof, whereas it is open at the distal end thereof. The terms "distal" and "proximal" refer to the ends of the device, or of a part or component thereof facing respectively the tip of the antenna or in an opposite direction.

Between the cylindrical conductor and the external conductor of the antenna one or more sleeves made of dielectric material are interposed that fill the entire length of the choke. The length of the choke is equal to an odd number (normally one) of wavelength quarters in said dielectric of the microwaves emitted by the antenna. Lengths that are very different from a wavelength quarter give the choke sub-optimal properties and nevertheless useful for the purpose of obtaining a proximal confinement and thus pronounced sphericity of the radiation figure of the antenna. The choke is usually obtained by inserting, around the dielectric that surrounds the external conductor of the antenna, a metal cylinder with an internal diameter that is equal to the external diameter of the dielectric and is of a length that is such as to make an electric length that is equivalent to what has already been disclosed. The end of the metal cylinder that is further from the radiant end of the antenna is short-circuited on the external conductor of the antenna, completing the structure of the choke.

A microwave device for tissue ablation of the type quoted above is disclosed in the Italian patent for industrial invention 0001361771 in the name of the applicant.

The dielectric has to be of a material that loses little to the microwaves. The most common materials with such characteristics are polymers and ceramics. The polymers are rarely used in antennas for thermoablation because the antenna can reach temperatures of several hundreds of degrees Celsius, at which all polymers known today melt or anyway lose their mechanical properties. Antennas for thermoablation are thus generally made by using ceramics as dielectric.

All antennas for thermoablation have a composite structure of the part designed to dispense the microwaves, in which there are different particular parts of different materials. Given the need for a very reduced overall transverse dimension, typically less than 3 mm, the particular parts that constitute the antenna have very thin thicknesses and extremely reduced joint surfaces. This generally makes the microwave antennas subject to mechanical breakages with subsequent detachment of the components during clinical use. In particular, this phenomenon can occur at the moment of extraction of the antenna from the patient if intense adhesion of the tissues to the antenna has occurred. In this case, the antenna can be subjected to traction of a few kilograms by the physician to obtain removal thereof.

The joints between the various metal parts can be obtained by brazing or mechanical interference, which is particularly easy to make between metal materials because of the malleability thereof. The most difficult joints between those normally found in antennas for thermoablation are normally those between the dielectric and the metal parts. As the joint is partially made of non-metal parts, brazing is impossible, which would enable junctions with resistance to traction to be obtained that is comparable to that of the materials that are connected. The joints between ceramics and metal are usually obtained in the antennas for thermoablation by gluing or mechanical interference. In the former case the joint is a weak point in the structure because glues generally tend to lose adhesiveness as the temperature rises. The estimated work temperature is in fact, as said, a few hundred degrees Celsius. Further, the gluing together of dissimilar materials such as the dielectric material and the external coaxial conductor or the metal cannula, is generally less strong than the gluing together of homogeneous parts (for example, metals). On the other hand, if the joint is obtained by mechanical interference, the overall transverse dimension of the antenna usually increases because ceramics are non-malleable materials and are therefore unsuitable for the crushing that is necessary to obtain satisfactory mechanical interference with a limited contact surface. In order to remedy this, locking by mechanical interference between ceramics and metal has to be obtained with devices of macroscopic dimensions, for example by bolting or punching, with a consequent increase in the transverse overall dimension of the applicator.

In addition to the sphericity of the radiation figure, the different types of microwave antenna are thus also characterised by the engineering solutions adopted to reach resistance to mechanical stress that is as great as possible.

The present invention proposes providing a microwave device for organic tissue ablation that has optimum sphericity of the radiation figure of the microwaves, great mechanical resistance and transverse dimensions that are as reduced as possible.

The object of the invention is achieved with a microwave device for the ablation of biological tissues comprising a coaxial antenna, said coaxial antenna comprising an internal conductor, surrounded by a layer of dielectric material, an external conductor that is externally coaxial to said layer of dielectric material, a metal tip that is connected electrically to said internal conductor, a quarter wave impedance transformer ending in a short circuit, said impedance transformer comprising a sleeve made of dielectric material having a proximal end covered with a layer of metal material obtained by depositing said metal material on the surface of said dielectric material, said layer of metal material extending for a length near a quarter of wavelength of the electromagnetic field in said dielectric material at the operating frequency of the device or of odd multiples of said quarter of wavelength, said layer of metal material being connected electrically to said external conductor, wherein it further comprises a metal cannula inserted above said sleeve, said metal cannula being connected to said layer of metal material by gluing, brazing, welding or mechanical interference.

Owing to the invention it is possible to obtain a microwave device for tissue ablation in which the transverse dimensions of the choke are minimised and the joints between the dielectric and the metal parts of the antenna have great mechanical resistance.

This result is obtained by making the choke by metallizing the surface of the dielectric made of ceramics, such metallisation being obtained by physical or chemical deposition of metal vapours on the surface of the ceramic material. The factor common to all the metallisations is a thickness of the metal layer of a few micrometres and a strong adhesion thereof to the ceramic substrate. This has two important advantages: the possibility of making chokes of minimum transverse dimensions owing to the minimum thickness of the metallisation layer, and the possibility of making joints between the ceramic dielectric and the metal parts of the antenna with great mechanical toughness that is greater than the solutions that are available on the market today. This is possible by exploiting the metallisation layer to make the aforesaid joints.

BRIEF DESCRIPTION OF THE DRAWINGS

Some embodiments of the invention are disclosed below merely by way of non-limiting example, with reference to the attached drawings, in which.

DETAILED DESCRIPTION OF THE INVENTION

Figure 1A:
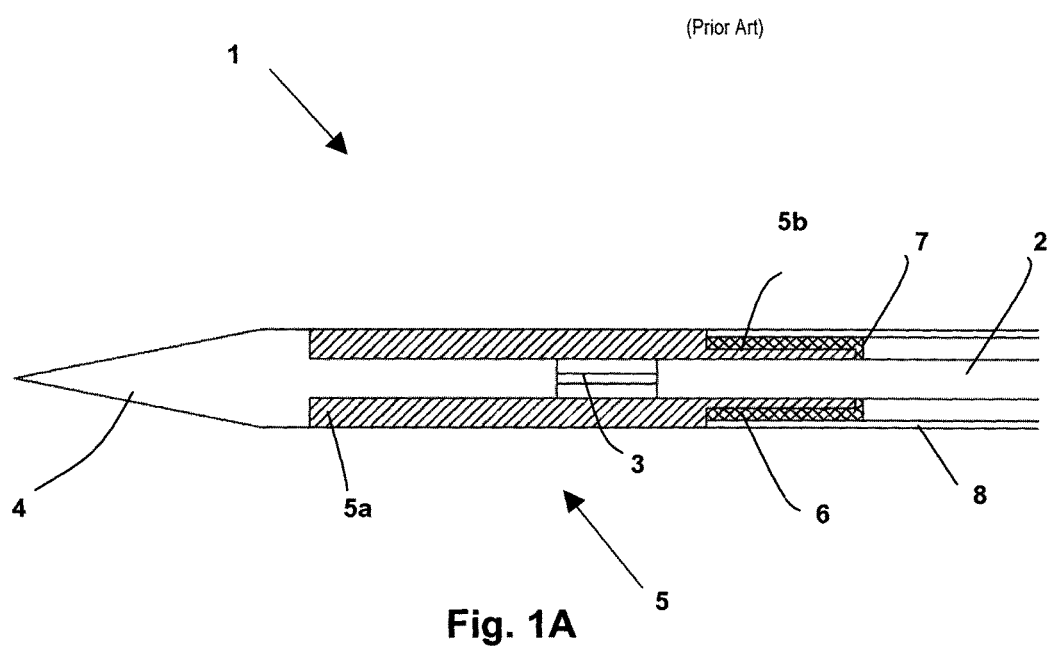
FIGS. 1A and 1B illustrate a microwave device for tissue ablation according to the prior art.
Figure 1B:
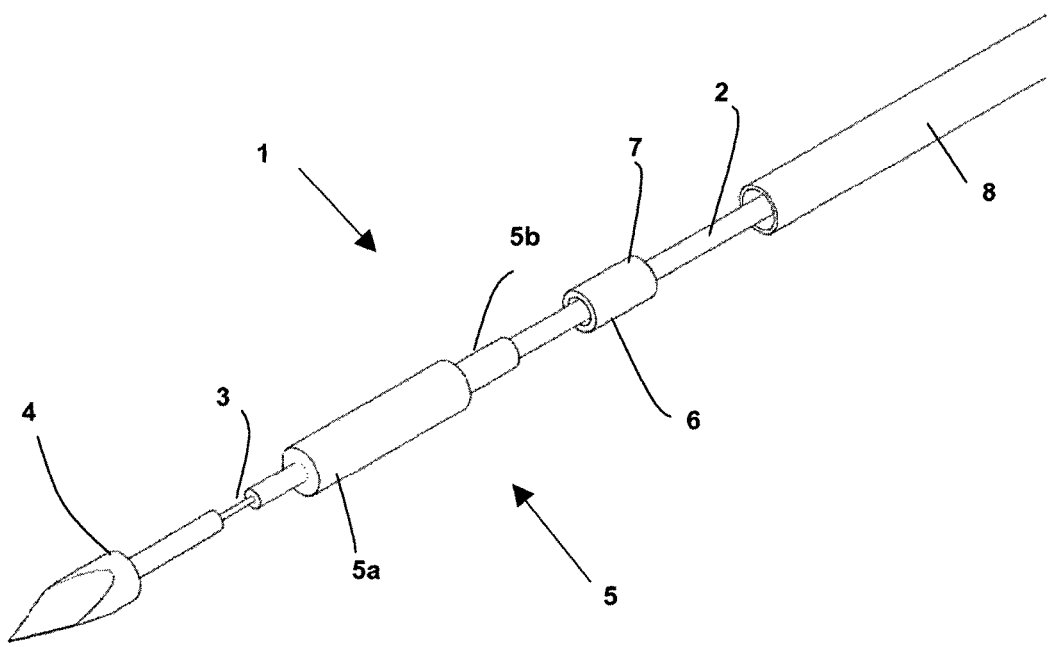
Figure 2A:
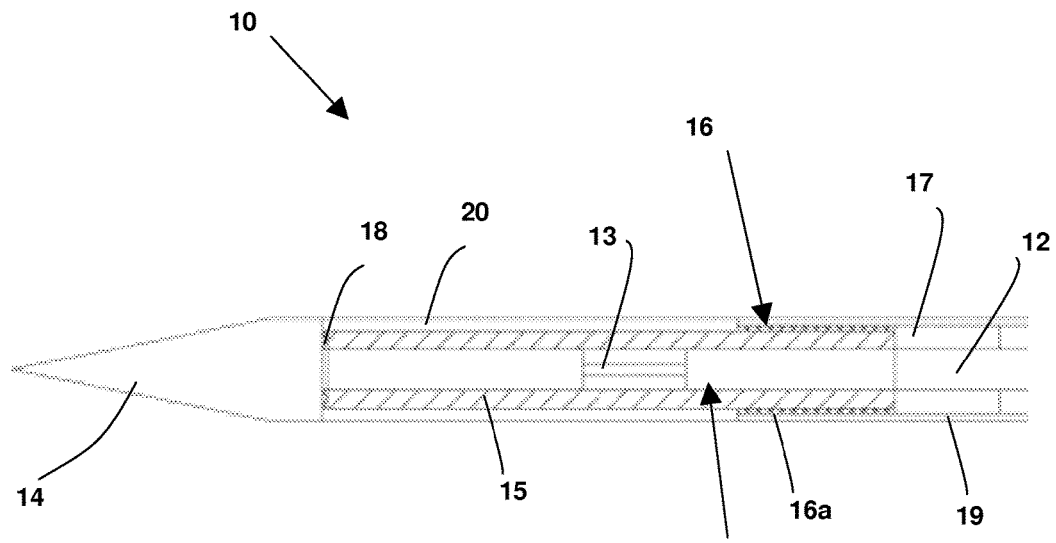
FIG. 2A is a longitudinal section view that illustrates a first embodiment of a microwave device for tissue ablation according to the invention.
Figure 2B:
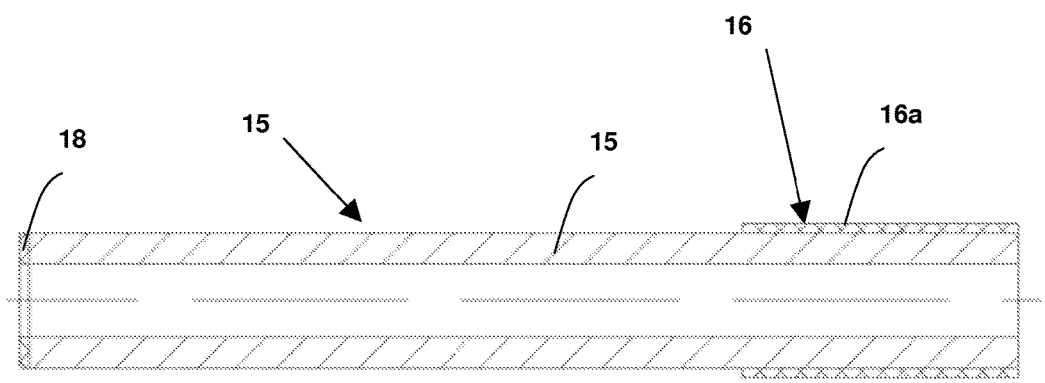
FIG. 2B is a longitudinal section view of a particular part of FIG. 2A.
Figure 2C:
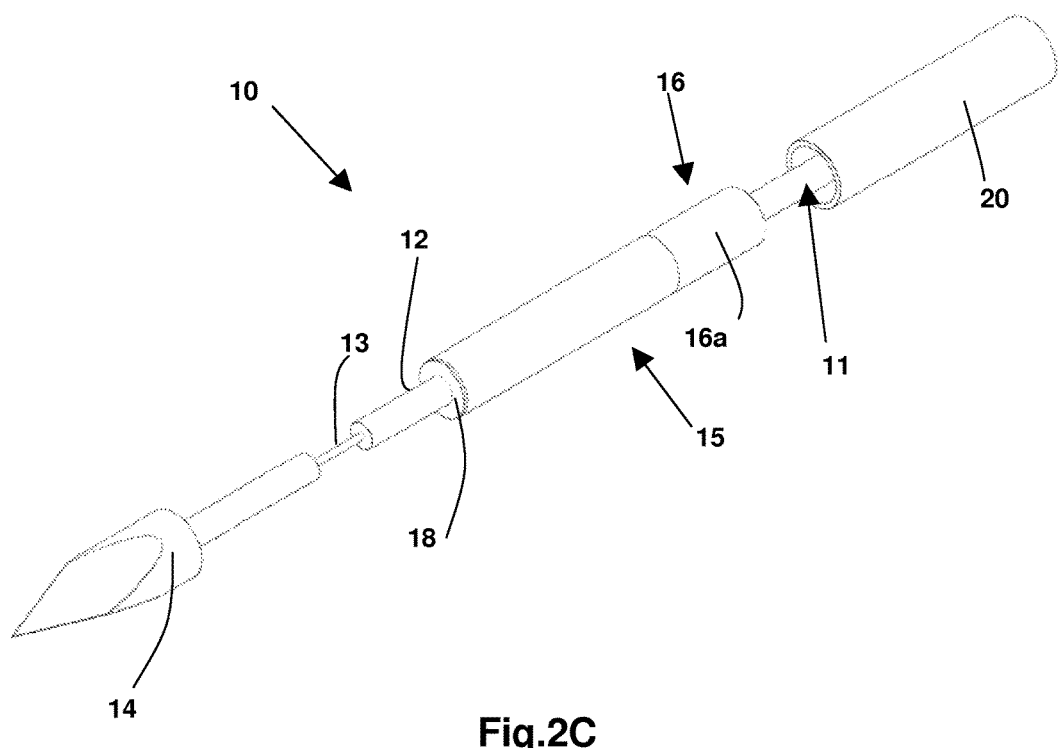
FIGS. 2C to 2F are perspective views that illustrate the first embodiment of a microwave device for tissue ablation according to the invention.
Figure 2D:
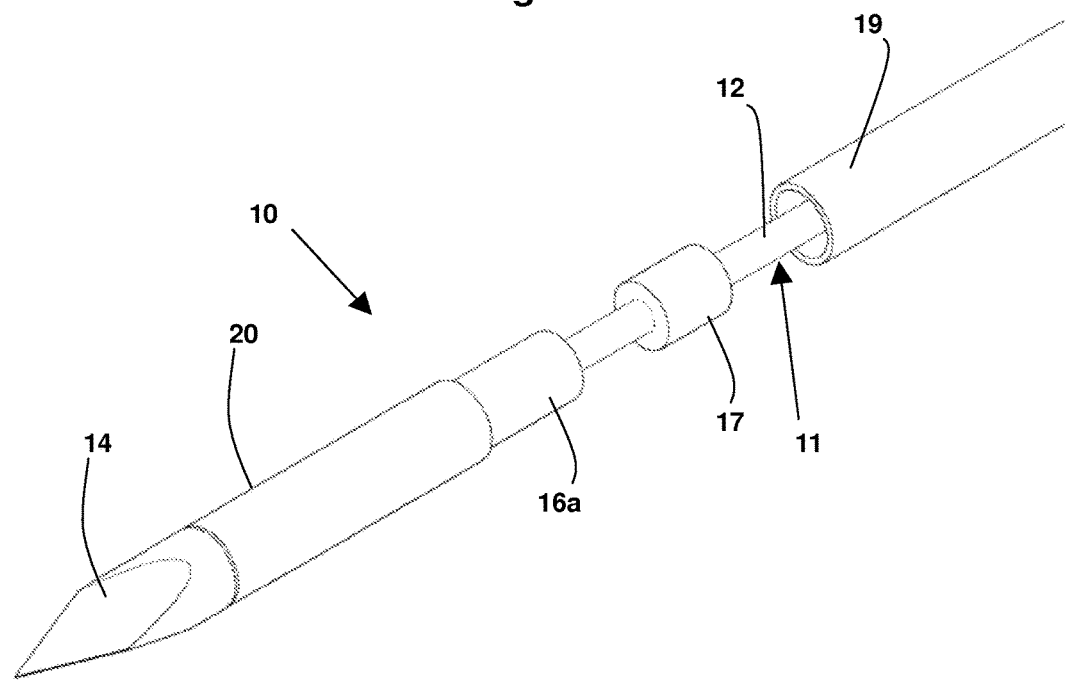
Figure 2E:
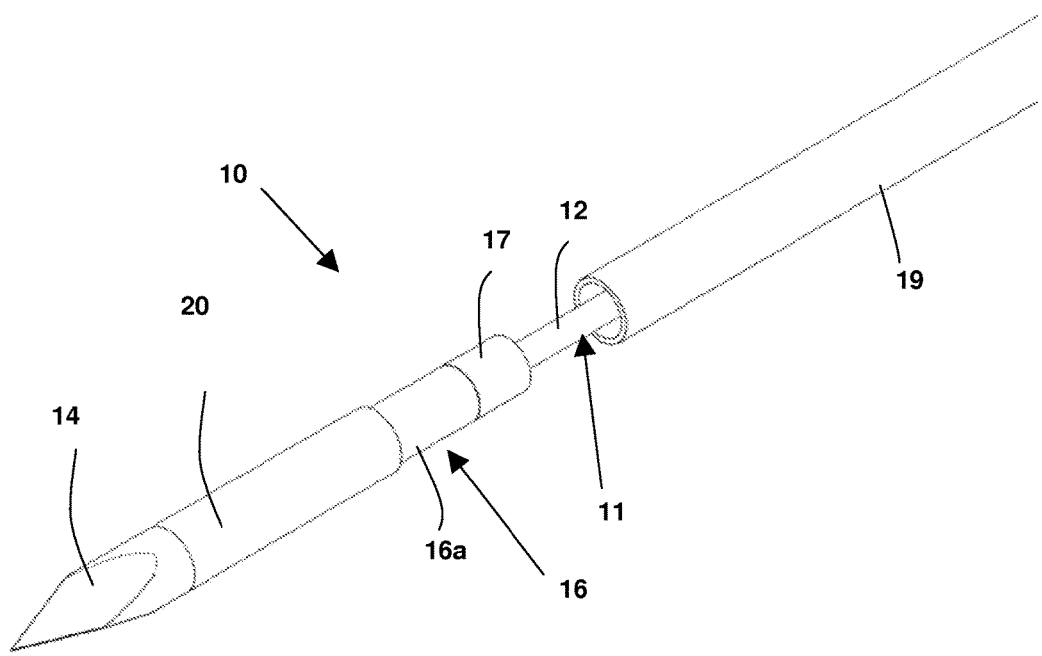
Figure 2F:
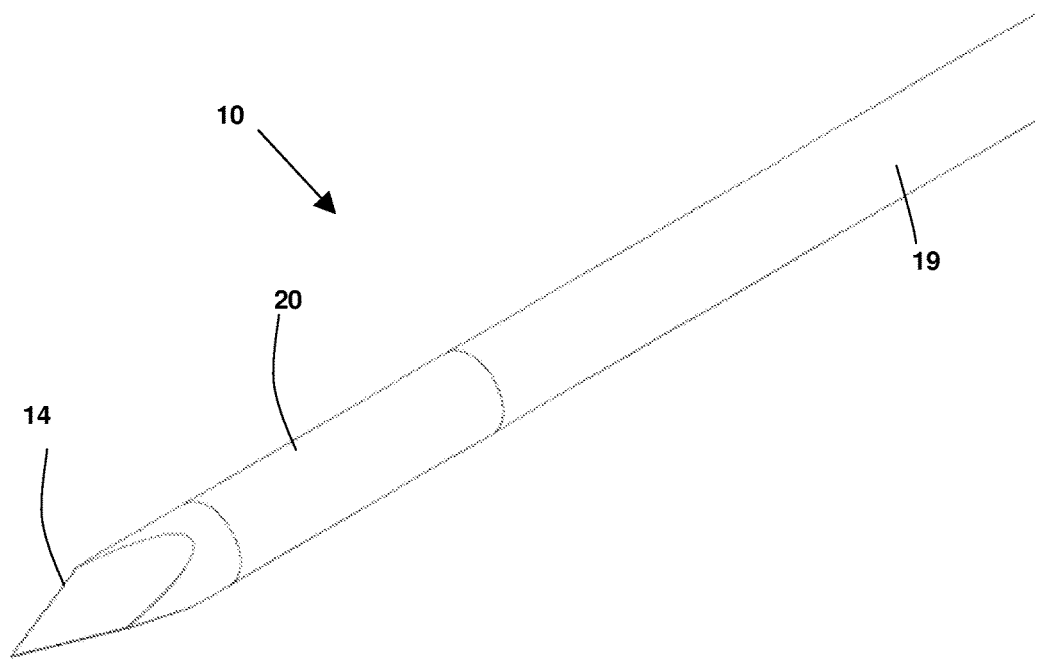
Figure 3A:
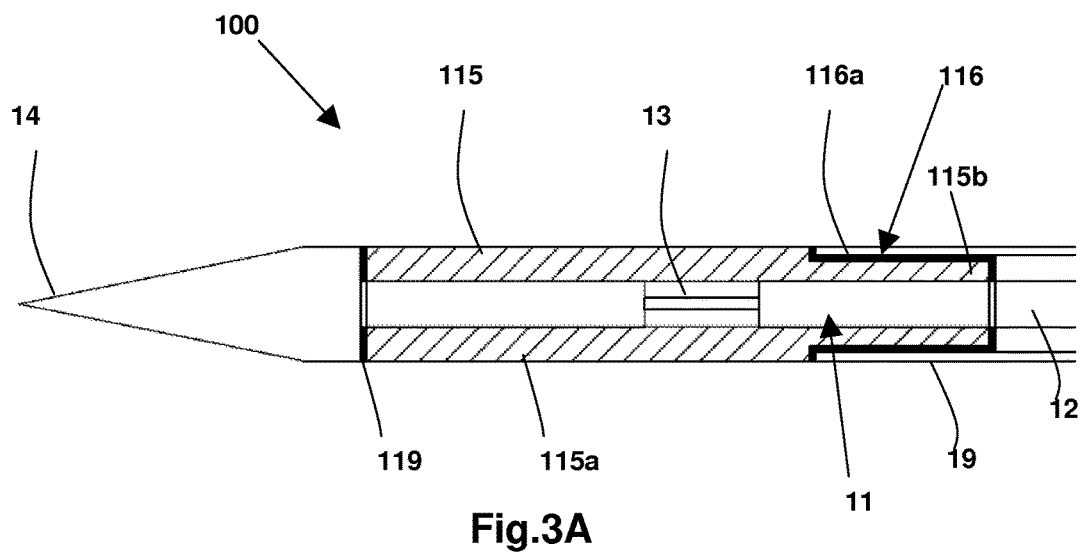
FIG. 3A is a longitudinal section view that illustrates a second embodiment of a microwave device for tissue ablation according to the invention.
Figure 3B:
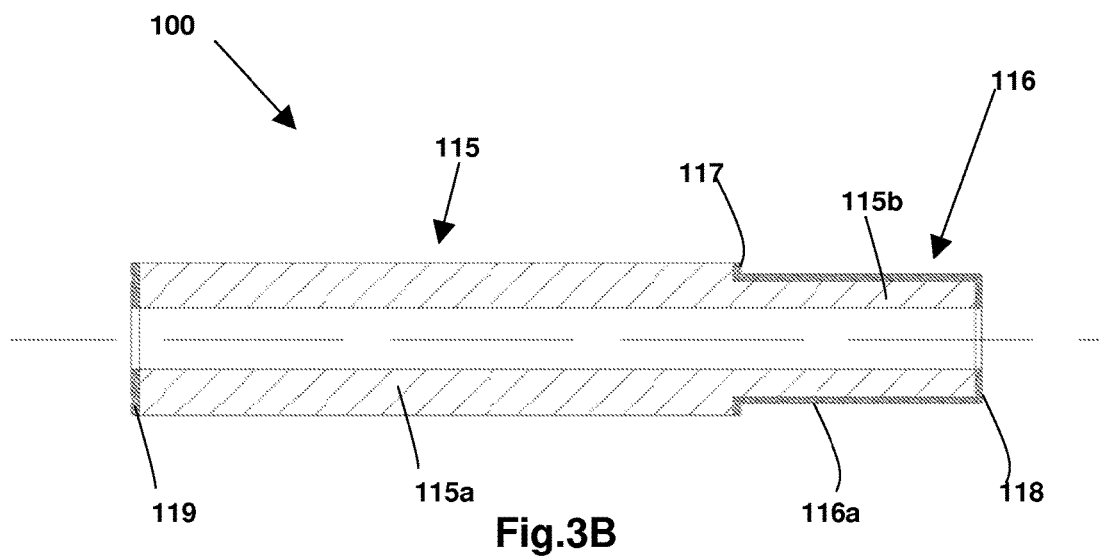
FIG. 3B is a longitudinal section view of a particular part of FIG. 3A.
Figure 3C:
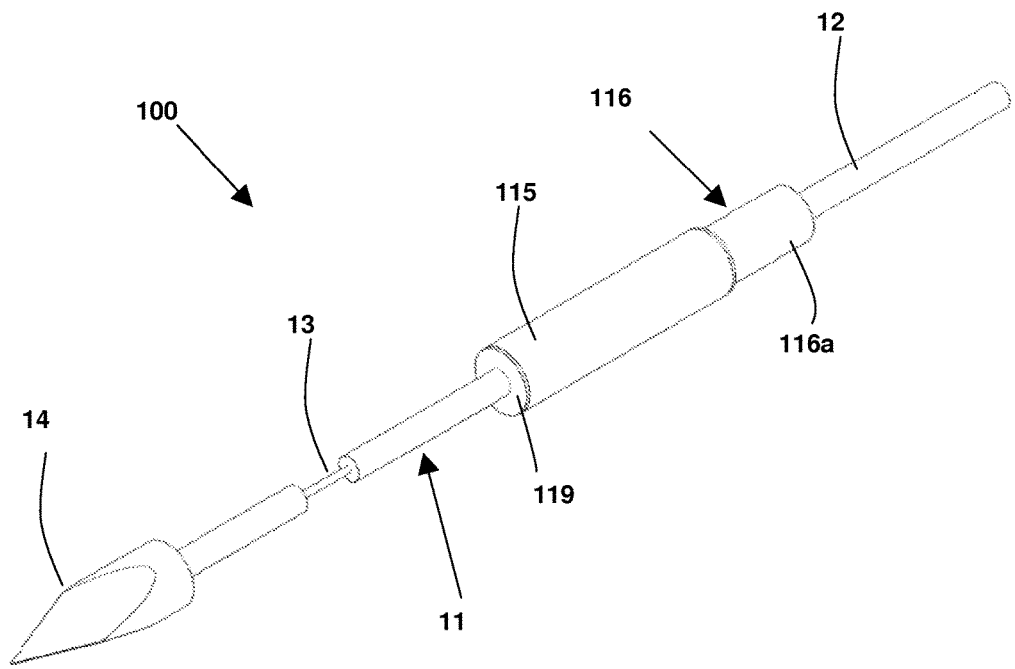
FIGS. 3C to 3E are perspective views that illustrate the second embodiment of a microwave device for tissue ablation according to the invention.
Figure 3D:
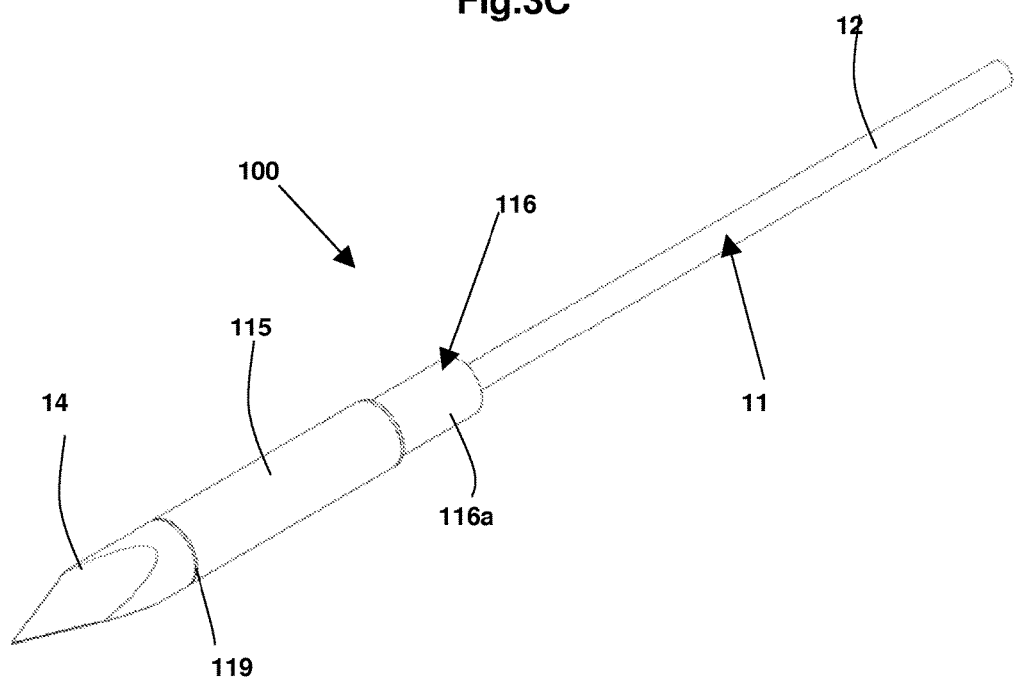
Figure 3E:
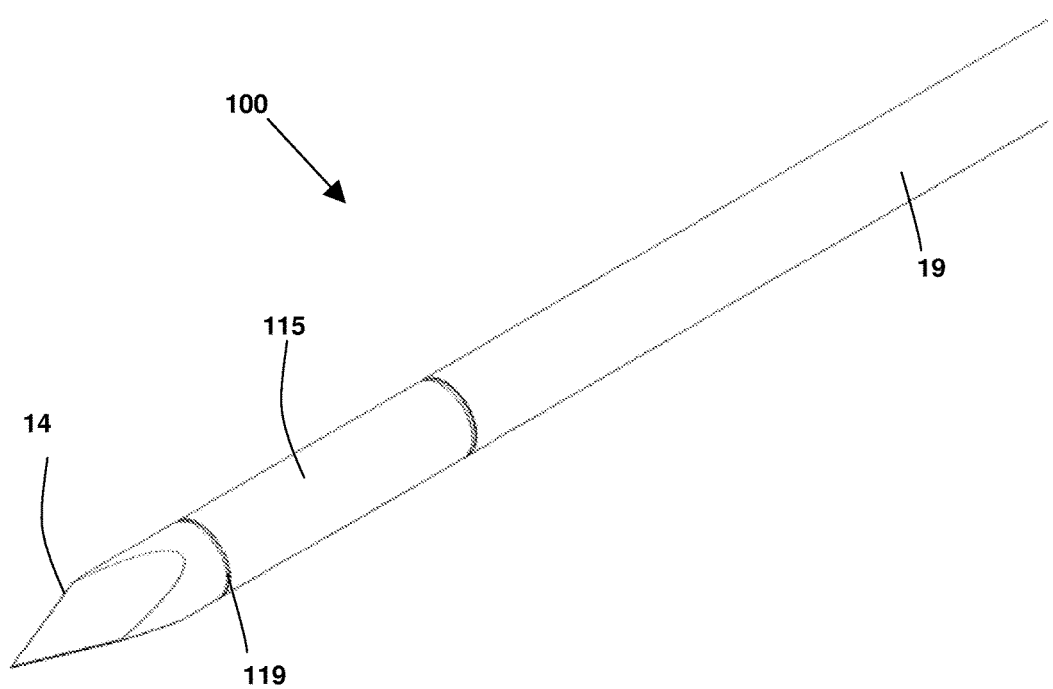

In FIGS. 1A to 1B a microwave device 1 for tissue ablation according to the prior art is illustrated that comprises:
  a coaxial antenna consisting of a external conductor 2 in the shape of a hollow cylinder, of a internal conductor 3 in the shape of a wire, arranged coaxially inside the external conductor 2 and of a dielectric insulating material, which is not visible in figures, interposed between the external conductor 2 and the internal conductor 3;
  a radiant part, consisting of a prolongation of the internal conductor 3 to which a metal tip 4, for example of conical shape, is fixed, to give the device 1 the ability to penetrate tissues;
  a first sleeve 5 made of dielectric material, for example a ceramic material, inserted onto the distal end of the external conductor 2 and fixed, at a distal end thereof, to the tip 4; the first sleeve 5 has a distal part 5a of a greater diameter and a proximal part 5b of a smaller diameter;
  a quarter wave impedance transformer, a so-called choke", consisting of a second sleeve 6 made of electrically conductive material, inserted coaxially on the proximal part 5b of the first sleeve 5 made of dielectric material, the proximal end 7 of the choke being closed in a short circuit on the external conductor 2 of the coaxial antenna;
  a protection cannula 8, that winds both the coaxial antenna and the choke to give mechanical toughness to the device 1.

A microwave device 1 for tissue ablation like the one illustrated in FIGS. 1A and 1B has two drawbacks. The first is that it is extremely difficult to make joints with great mechanical resistance between the components of the device. In particular, the joints between the first sleeve 5 made of ceramic material and the metal tip 4, between the second sleeve 6 made of electrically conductive material, constituting the choke, and the distal part 5a of the first sleeve 5 and between the cannula and the first distal part 5a of the first sleeve 5 are critical. In fact, it is not possible to make said joints by welding because of the presence of the first sleeve 5 made of ceramic material and it is therefore necessary to resort to joints by gluing that have much lower mechanical resistance than joints made by welding.

The second drawback of applicators for thermoablation designed according to the model of FIGS. 1A and 1B, is that making the choke entails a relatively wide cross section thereof.

Both the aforesaid drawbacks are overcome in a microwave device for tissue ablation according to the invention.

A first embodiment of a microwave device 10 for tissue ablation is shown in FIGS. 2A to 2F.

The device 10 according to the invention comprises a coaxial antenna 11 consisting of an external conductor 12 and of an internal conductor 13, coaxial to the external conductor 12, a dielectric material that is not shown in the Figure being interposed between the internal conductor 13 and external conductor 12.

The internal conductor 13 is connected, at the distal end thereof, to a tip 14, for example of conical shape, that is suitable for facilitating the penetration of the device 10 into the tissues of the body of a patient.

On the external conductor 12 of the coaxial antenna 11 a sleeve 15 is inserted that is made of a dielectric material, for example a ceramic material that is resistant to high temperatures.

At the proximal end of the sleeve 15 a quarter wave impedance transformer 16 is made, so-called choke, metallising the external surface of said proximal end by depositing thereupon a thin layer 16a of metal material, i.e. of an electrically conductive material.

The metal material can be deposited by physical or chemical deposition of vapours of said metal material.

Metallisation of the external surface of said proximal end extends over a length that is equal to a quarter of wavelength of the electromagnetic field at the operating frequency of the device 10 or of odd multiples of said quarter of wavelength, such as to ensure appropriate confinement of the retrograde surface currents and consequently greater sphericity of the radiation figure of the antenna 11. As chokes of nearly but not exactly the same length as the choke quoted above also enable an almost spherical radiation Figure to be obtained it is intended that the proposed invention includes the creation, by metallisation of said sleeve 15, of impedance transformers, or chokes, of nearly but not exactly the same length as a quarter of wavelength of the electromagnetic field at the operating frequency of the device 10 or of odd multiples of said quarter of wavelength. The short circuit of the choke can be made by a metal cylinder 17, inserted onto the external conductor 12 of the coaxial antenna, in contact with said proximal end of the sleeve 15, and connected electrically with the external conductor 12 of the coaxial antenna 11 and with said layer 16a of metal material.

In order to minimise the overall transverse dimension of the choke 16, it is possible to make the metallisation layer 16a with a thickness that is equal to the minimum required to ensure an almost ideal reflection of the microwaves. It is known that at the interface with a dielectric and a metal the microwaves penetrate inside the metal for a few micrometres, undergoing an exponential attenuation. This pattern is characterised by a length, known as "penetration length", defined as the distance between the dielectric/metal interface and the point inside the metal in which the intensity of the electric field is reduced by a factor equal to the number e (Nepero number) with respect to the intensity of the electric field at said interface. In order to obtain the choke effect, it is sufficient for the thickness of the layer 16a of metal to be equal to a few penetration lengths, for example three. The thickness of the choke will thus be a few microns, with respect to a thickness of a few tenths of a millimetre of the chokes of the devices known from the prior art.

This result is obtainable only through the technique of depositing metal on the surface of the ceramics disclosed above and enables a choke to be constructed the overall transverse dimension of which is the least possible: this particular implementation of a choke known as a micro-choke is defined below.

Also the distal end of the sleeve 15 is covered with a layer of metal 18, such layer of metal being deposited with the same technique used to make the micro-choke 16. The layer of metal 18 is used to connect the sleeve 15 to the tip 14 by welding, so as to make a connection with great mechanical resistance.

The device 10 is completed by a metal cannula 19 inserted above said sleeve 15, and possible by a second cannula 20 made of non-stick plastics interposed between the cannula 19 and the tip 14 of the device 10.

If the short circuit of the choke is made by the metal cylinder 17, the latter can be provided with hydraulic seal systems between the metal cylinder 17 and the cannula 19. In fact, the circulation inside the device 10 of a coolant is required for removing the heat produced both by the dissipation of power along the coaxial antenna 11, and by the interaction of the microwaves with the organic tissues. The hydraulic seal between the metal cylinder 17 and the cannula 19 is used to prevent the coolant being able to escape from the device 10 and spill into the surrounding tissues.

The metal cannula 19 can be fixed to the layer 16a of metal material by gluing, brazing or mechanical interference, for example crimping, said layer 16a of metal material making a hydraulic seal with the cannula 19.

In FIGS. 3A to 3E a second embodiment of a microwave device 100 according to the invention is illustrated. The details of this second embodiment are the same as those disclosed in FIGS. 2A to 2F with reference to the first embodiment 10 of the microwave device according to the invention are indicated by the same reference numbers.

Similarly to the device 10 disclosed above, the device 100 comprises coaxial antenna 11 consisting of an external conductor 12 and of an internal conductor 13, coaxial to the external conductor 12, a dielectric material being interposed between the internal conductor 13 and the external conductor 12.

The internal conductor 13 is connected, at the distal end thereof, to a tip 14, for example of conical shape, that is suitable for facilitating the penetration of the device 100 into the tissues of the body of a patient.

On the external conductor 12 of the coaxial antenna 11 a sleeve 115 is inserted that is made of dielectric material, for example a ceramic material that is resistant to high temperatures.

The sleeve 115 consists of a first distal part 115a and of a second proximal part 115b having different diameters, the first part 115a having a greater diameter than the second part 115b.

The second part 115b and a portion of the first part 115a adjacent to the second part 115b are covered by a layer 116a of metal material obtained from physical or chemical deposition of vapours of said metal material. The layer of metal material 116 constitutes the quarter wave impedance transformer, or choke, disclosed previously, made with the same criteria disclosed previously.

The layer of metal material 116a also extends on the linking surface 117 between the first part 115a and the second part 115b of the sleeve 115.

Further, the layer of metal material 116a also extends over the front surface 118 of the proximal end of the sleeve 115, until it comes into contact with the external conductor 12 of the coaxial antenna 11, to make the short circuit of the choke. The short circuit can be made by electrically connecting the layer of metal material 116a to the external conductor 12 by welding.

At the distal end of the sleeve 115, intended to be connected to the tip 14, a second layer 119 of metal material is made that is made in a similar manner to the layer 116a. The second layer 119 is used to permit a connection between welding between the sleeve 115 and the metal tip 14, in such a manner as to obtain a connection with great mechanical resistance.

The device 100 is completed by a cannula 19 in metal material that is inserted above the second part 115b of the sleeve 115 until it comes to abut on the metallised linking surface 117 and is fixed by welding, gluing or mechanical interference, for example crimping, to the layer 116a of metal material to obtain a connection that guarantees a hydraulic seal between the cannula 19 and the sleeve 115 to prevent cooling liquid being able to infiltrate between the cannula 20 and the sleeve 115.

In the practical embodiment the materials, dimensions and constructional details can be different from those indicated but be technically equivalent thereto without thereby falling outside the scope of the present invention.

The invention claimed is:

1. A microwave device for ablation of biological tissues comprising a coaxial antenna, said coaxial antenna comprising an internal conductor, surrounded by a layer of dielectric material, an external conductor that is externally coaxial to said layer of dielectric material, a metal tip that is connected electrically to said internal conductor, a quarter wave impedance transformer closed in a short circuit on the external conductor of the coaxial antenna, said quarter wave impedance transformer comprising a sleeve made of a dielectric material having a proximal end covered with a layer of metal material obtained by depositing said metal material on an external surface of said dielectric material, said layer of metal material extending for a length near a quarter of wavelength of an electromagnetic wave in said dielectric material at an operating frequency of the microwave device or of odd multiples of said quarter wavelength of the electromagnetic wave, said layer of metal material being connected electrically to said external conductor, a metal cannula inserted above said sleeve, said metal cannula being directly affixed to said layer of metal material whereby the metal cannula is hydraulically sealed to said sleeve, wherein said sleeve made of dielectric material comprises a first distal part having a first diameter and a second proximal part having a second diameter, said first diameter being greater than the second diameter, said layer of metal material extending over said second proximal part and over a portion of said first distal part adjacent to said second proximal part.

2. The microwave device, according to claim 1, wherein said dielectric material is a ceramic material.

3. The microwave device according to claim 1, wherein said layer of metal material is made by physical or chemical deposition of vapours of said metal material on the surface of said sleeve.

4. The microwave device, according to claim 1, wherein said layer of metal material has a thickness that is at least three times a penetration length of said microwaves in said metal material, at an interface between said metal material and said dielectric material.

5. The microwave device, according to claim 1, further comprising a metal cylinder, inserted onto the external conductor of the coaxial antenna, in contact with said proximal end of the sleeve made of dielectric material, said metal cylinder being connected electrically to said external conductor and to said layer of metal material.

6. The microwave device, according to claim 5, wherein said metal cylinder is hydraulically sealed to said metal cannula.

7. The microwave device, according to claim 1, further comprising a second cannula made of non-stick plastics, said second cannula being able to be interposed between said metal cannula and said metal tip.

8. The microwave device according to claim 1 wherein said further layer of metal material is connected by brazing, welding, mechanical interference or gluing to said metal tip.

9. The microwave device, according to claim 1, wherein said layer of metal material also extends over a linking surface between the first distal part and the second proximal part.

10. The microwave device, according to claim 9, wherein said cannula made of metal material is positioned above the second proximal part of the sleeve and configured to abut on the linking surface.

11. The microwave device, according to claim 1, wherein said layer of metal material also extends over a front surface of the proximal end of the sleeve and is connected electrically to said external conductor.

12. The microwave device, according to claim 1, wherein a distal end of the sleeve is connected to the metal tip by depositing a second thin layer of metal material.

13. The microwave device, according to claim 12, wherein said second layer of metal material is connected to said metal tip by brazing, welding, mechanical interference or gluing.

* * * * *